(12) United States Patent
Ishizaka et al.

(10) Patent No.: US 6,395,917 B1
(45) Date of Patent: May 28, 2002

(54) PREPARATION OF ORGANOHALOSILANES

(75) Inventors: Hajime Ishizaka; Susumu Ueno; Toshio Shinohara, all of Annaka; Yoichi Tanifuji, Tokyo; Tetsuya Inukai; Mikio Aramata, both of Annaka, all of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/981,822

(22) Filed: Oct. 19, 2001

(30) Foreign Application Priority Data

Oct. 20, 2000 (JP) .......................................... 2000-320538

(51) Int. Cl.$^7$ .................................................. C07F 7/16
(52) U.S. Cl. ....................................................... 556/472
(58) Field of Search ........................................... 556/472

(56) References Cited

U.S. PATENT DOCUMENTS

| | | | |
|---|---|---|---|
| 2,380,995 A | | 8/1945 | Rochow |
| 4,554,370 A | * | 11/1985 | Ward et al. .................. 556/472 |
| 5,250,716 A | * | 10/1993 | Mui ............................. 556/472 |
| 5,312,948 A | * | 5/1994 | Freeburne et al. .......... 556/472 |
| 6,175,030 B1 | * | 1/2001 | Kalchauer et al. .......... 556/472 |
| 6,239,304 B1 | * | 5/2001 | Aramata et al. ............. 556/472 |

FOREIGN PATENT DOCUMENTS

| DE | 199 19 337 C1 | 4/1999 |
|---|---|---|
| JP | 61-112085 A | 5/1986 |
| JP | 0 256 876 A2 | 2/1988 |
| JP | 4-59318 B2 | 9/1992 |

* cited by examiner

*Primary Examiner*—Paul F. Shaver
(74) *Attorney, Agent, or Firm*—Birch, Stewart, Kolasch & Birch, LLP

(57) ABSTRACT

When oganohalosilanes are prepared by charging a reactor with a contact mass containing a metallic silicon powder, a copper catalyst and a co-catalyst, and introducing an organohalide-containing gas into the reactor to effect the direct reaction, the catalyst and/or co-catalyst used in the contact mass is obtained by mixing particles of the catalyst and/or co-catalyst with finely divided silica, and applying shear forces to the mixture for mutually rubbing the particles, thereby producing the catalyst and/or co-catalyst having finely divided silica fused to surfaces thereof. The invention is successful in producing organohalosilanes at a significantly improved formation rate without reducing the proportion of diorganodihalosilane.

5 Claims, 2 Drawing Sheets

ROTATIONAL DIRECTION

PREPARATION OF ORGANOHALOSILANES

This invention relates to an industrial process for preparing organohalosilanes.

BACKGROUND OF THE INVENTION

With respect to the synthesis of alkylhalosilanes, E. Rochow first disclosed in U.S. Pat. No. 2,380,995 direct synthesis reaction between metallic silicon and alkyl halide in the presence of a copper catalyst. Since then, there have been reported a number of research works relating to various co-catalysts used together with copper catalysts, reactors, additives used during reaction, and the like.

In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silanes produced and a T/D ratio. Organohalosilane products contain diorganodihalosilane (D), triorganohalosilane (M), organotrihalosilane (T), etc. as well as other by-products such as organohydrodihalosilane (H) and organohalodisilane. In particular, disilanes are known as a high-boiling fraction among manufacturers who make silicones from organohalosilanes obtained by the direct process, because few processes are available for the effective utilization of disilanes, and most disilanes are discarded. The T/D ratio is a compositional ratio of organotrihalosilane to diorganodihalosilane in the entire organohalosilanes produced, with a lower T/D ratio being preferred.

The formation rate of organohalosilane is represented by a space time yield (STY) which is the weight of crude organohalosilane produced per unit time relative to the weight of metallic silicon held in the reactor. In order to improve the content of diorganodihalosilane produced, reduce the T/D ratio or increase the STY, various research works have been made with a focus on the catalyst and co-catalyst. Also, an attempt was made to add an inert solid to the reactor for improving the results of organohalosilane synthesis.

JP-A 61-112085 discloses to add fumed silica to a fluidized bed reactor for the purpose of reducing agglomeration of cuprous chloride within the reactor.

JP-B 4-59318 discloses, for the production of halogen-bearing silanes, to add inert solid particles having a particle size distribution in the range of 20 to 450 μm to a fluidized bed reactor for the purpose of facilitating the temperature control of the reaction zone within the reactor.

German Patent No. 19919337C1 discloses to use metallic silicon, copper catalyst, zinc co-catalyst and fumed silica for the purpose of reducing the amount of the catalyst used to produce methylchlorosilane.

As discussed above, it is economically advantageous for the industrial production of organohalosilanes to improve the proportion of diorganodihalosilane produced and increase the formation rate of organohalosilanes. However, these two targets are in a tradeoff relationship. An attempt to improve either one of the targets results in a failure to improve the other target. It has been an outstanding issue for engineers to find a solution to overcome the tradeoff phenomenon.

SUMMARY OF THE INVENTION

An object of the invention is to provide a process for producing organohalosilanes which process can increase the formation rate of organohalosilanes without reducing the proportion of diorganodihalosilane produced.

The inventors have found that by mixing particles of a catalyst and/or a co-catalyst with finely divided silica, mechanically applying shear forces to the mixture for mutually rubbing the particles, thereby producing the catalyst and/or co-catalyst having finely divided silica attached to surfaces thereof, and using the resulting catalyst and/or co-catalyst in a contact mass, quite unexpectedly, the formation rate of organohalosilanes can be improved without reducing the proportion of diorganodihalosilane produced.

After catalyst particles and/or co-catalyst particles and finely divided silica are rubbed under the mechanical application of shear forces, the catalyst and/or co-catalyst is used for the synthesis of organohalosilanes. Quite unexpectedly, unlike a simple mixture, the mechanically rubbed mixture is effective for substantially improving the reactivity of organohalosilane synthesis.

Although the mechanism by which reactivity is improved is not well understood, it is presumed that when finely divided silica is rubbed against surfaces of catalyst or co-catalyst particles under shear forces, fusion between the catalyst or co-catalyst surfaces and finely divided silica surfaces, which is referred to as "mechanical alloying," occurs. This modifies the physical and chemical characteristics of the catalyst or co-catalyst, as a result of which the formation rate of organohalosilane is significantly increased. Presumably, changes of the shape of catalyst or co-catalyst particles, changes of the surface topography of catalyst or co-catalyst particles, and changes of other factors by the mechanical effects cooperate with changes of the catalysis by the mechanochemical effects, in a complex manner to bring about an increased formation rate of organohalosilanes. The modification of catalysis by such shear force-applying operation is a unique effect that does not occur by merely mixing the catalyst with finely divided silica, but occurs only when shear forces are imparted, as will be demonstrated by Examples to be described later.

Accordingly, the present invention provides a process for preparing oganohalosilanes comprising the steps of charging a reactor with a contact mass containing a metallic silicon powder, a copper catalyst and a co-catalyst, and introducing an organohalide-containing gas into the reactor to effect reaction to form organohalosilanes of the following general formula (1):

$$R_n(H)_m SiX_{(4-n-m)} \tag{1}$$

wherein R is a monovalent hydrocarbon group of 1 to 6 carbon atoms, X is a halogen atom, n and m each are an integer of 0 to 3, and the sum of n and m is 1 to 3, the process further comprising the steps of mixing particles of the catalyst and/or co-catalyst with finely divided silica, and mechanically applying shear forces to the mixture for mutually rubbing the particles, thereby producing the catalyst and/or co-catalyst having finely divided silica attached to surfaces thereof, which is used in the contact mass.

DESCRIPTION OF THE PREFERRED EMBODIMENT

Figure 1:
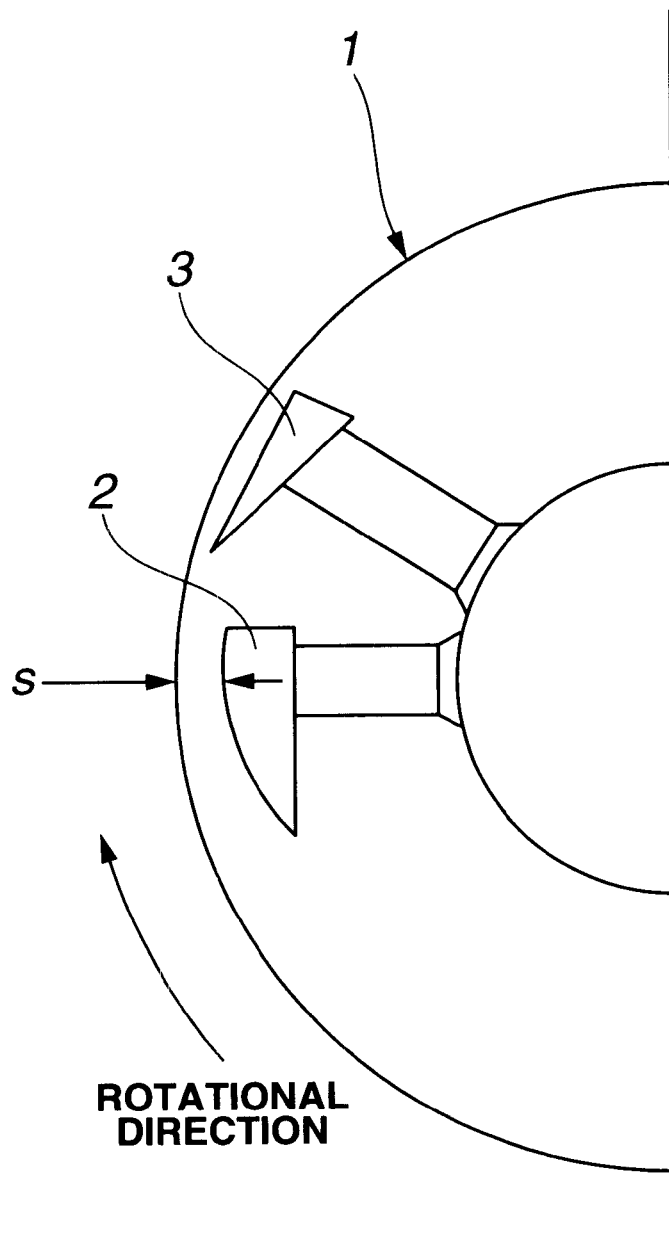
FIG. 1 schematically illustrates a mechanofusion apparatus.

According to the present invention, oganohalosilanes are prepared by charging a reactor with a contact mass containing a metallic silicon powder as well as a particulate copper catalyst and a particulate co-catalyst, at least one of which has finely divided silica mechanically smeared on surfaces thereof, and introducing an organohalide-containing gas into the reactor to effect reaction to form organohalosilanes of the following general formula (1):

$$R_n(H)_m SiX_{(4-n-m)} \tag{1}$$

wherein R is a monovalent hydrocarbon group of 1 to 6 carbon atoms, X is a halogen atom, n and m each are an integer of 0 to 3, and the sum of n+m is 1 to 3.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 µm, corresponding to 50% of the weight-base cumulative size distribution curve on sieving, in order that the metallic silicon powder have good fluidity.

The copper catalyst used herein may be selected from various forms of copper including elemental copper (or metallic copper) such as powdered copper and stamped copper, cuprous oxide, cupric oxide, copper halides such as copper chloride, and copper compounds such as copper acetate. Any of promoters such as zinc, tin, antimony, arsenic and phosphor may be used as the co-catalyst. The co-catalyst may be used alone or in the form of an alloy with copper. Exemplary copper alloys are Cu—Zn, Cu—Sn, and Cu—Zn—Sn (or Sb, As or P). Examples of the co-catalyst which is used alone include metallic zinc, zinc compounds such as zinc chloride, zinc oxide, and zinc acetate, metallic tin, tin compounds such as tin chloride and tin oxide, metallic antimony, antimony compounds such as antimony chloride and antimony oxide, metallic aluminum, aluminum compounds such as aluminum chloride and aluminum oxide, metallic phosphorus, inorganic phosphorus compounds such as copper phosphide, phosphorus trichloride and phosphorus oxide.

An appropriate amount of the copper catalyst blended is about 0.1 to 10 parts, and more preferably about 2 to 8 parts by weight per 100 parts by weight of the metallic silicon powder. The amount of the co-catalyst blended is suitably determined among the commonly used amounts depending on its type and form. For example, zinc is used in an amount of 0.05 to 1 part by weight per 100 parts by weight of the metallic silicon powder. Tin, antimony and arsenic are used in a single or total amount of 0.001 to 0.05 part, especially 0.005 to 0.01 part by weight per 100 parts by weight of the metallic silicon powder.

The organohalide to be reacted with metallic silicon to form organohalosilanes of the formula (1) is selected depending on the type of the desired organohalosilane product, that is, the type of R in formula (1) wherein R is a monovalent hydrocarbon group of 1 to 6 carbon atoms, typically an alkyl or aryl group. Illustrative examples of the organohalide include methyl chloride, ethyl chloride, propyl chloride, methyl bromide, ethyl bromide, benzene chloride and benzene bromide. Of these, methyl chloride and benzene chloride are preferable. Methyl chloride is most useful in the industry because dimethyldichlorosilane produced therefrom finds a wide variety of applications as the raw material for many silicone resins. The organohalide is previously heated and gasified before it is admitted into the reactor. The organohalide gas may be fed alone or combined with an inert gas in a sufficient amount to fluidize the contact mass, the fluidizing amount being determined as appropriate from the diameter of the reactor and the superficial velocity.

According to the invention, for the purpose of improving reactivity, shear forces are mechanically applied to a mixture of particles of the catalyst and/or co-catalyst and finely divided silica for rubbing the particles with each other, for thereby obtaining the catalyst and/or co-catalyst having finely divided silica attached or fused to surfaces thereof, which is used for the synthesis of organohalosilanes.

The procedure of mechanically rubbing finely divided silica to surfaces of catalyst or co-catalyst particles is not critical. Preferably an apparatus which can apply shear forces for effectively rubbing finely divided silica to surfaces of catalyst or co-catalyst particles is used. Such shear force-applying apparatus include a mechanofusion device, ball mill, media agitating mill, planetary mill, high-speed rotary type grinding machine, jet mill, shear mill and roller mill. Of these, the mechanofusion device, ball mill and shear mill are preferred.

Referring to FIG. 1, a mechanofusion device (AM-15F) is schematically illustrated. The device includes a rotating casing 1 and a stationary support having inner pieces 2 and scrapers 3 mounted thereon (only one set of an inner piece and a scraper is shown). The scraper 3 is located downstream of the inner piece 2 with respect to the rotating direction of the casing 1. Raw material (catalyst or co-catalyst particles and finely divided silica) is admitted into the casing 1. The casing 1 is rotated to centrifugally push the raw material against the inner wall of the casing 1 and shear forces are applied to the raw material between the inner piece 2 and the casing 1 whereby the finely divided silica is smeared and attached to surfaces of the catalyst or co-catalyst particles. The raw material modified between the casing 1 inner wall and the inner piece 2 is scraped off by the scraper 3. In this way, the operation of applying shear forces to the raw material is repeated. It is noted that the casing 1 is cooled in order to avoid any abnormal temperature rise by frictional heat. Namely, the mechanofusion device has the rotating casing 1 and the stationary inner piece 2 which cooperate to apply compression, shear and grinding actions to powder particles. The scraper 3 serves to scrape off the powder compressed between the inner piece 2 and the casing 1. The device is capable of applying mechanical energy to particles of a single material or plural materials to achieve (1) surface fusion, (2) dispersion and mixing, and (3) particle size control.

It is understood that actual operation is carried out by monitoring the power to the motor and the temperature of the powder particles at the inner piece.

The number of revolutions of the casing 1 and the clearance S between the casing 1 and the inner piece 2 are properly selected. It is preferred for the AM-15F mechanofusion device that the casing 1 be rotated at 300 to 3,000 rpm, and especially 800 to 2,200 rpm, and the clearance be set at 0.1 to 10 mm, and especially 0.5 to 5 mm.

The rubbing should preferably be carried out in a non-oxidizing atmosphere, such as nitrogen gas, argon gas, hydrogen gas or a mixture thereof.

The proportion of the catalyst and/or co-catalyst particles and the finely divided silica blended varies with the specific surface area thereof. Preferably the weight ratio of the catalyst and/or co-catalyst particles to the finely divided silica is from 1,000:1 to 10:1, more preferably from 200:1 to 20:1, and most preferably from 150:1 to 50:1.

The finely divided silica used herein is typically fumed silica or precipitated silica, though not limited thereto. Such silica is preferably hydrophobized, that is, treated with methyl or similar groups to be hydrophobic. The silica preferably has a specific surface area of about 50 to 400 $m^2/g$, and especially about 100 to 300 $m^2/g$.

When the catalyst and/or co-catalyst particles having finely divided silica mechanically smeared to surfaces thereof are observed under a scanning electron microscope (SEM), it is ascertained that the particle surfaces are covered with finely divided silica. Contrary to expectation, the coverage with finely divided silica does not detract from the reactivity of the catalyst and/or co-catalyst particles as will be demonstrated by Examples to be described later.

In the step of heating the contact mass or imparting catalytic activity to the contact mass, an inert gas is used for fluidizing the contact mass in the reactor. Such an inert gas may be nitrogen, helium or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas and the organohalide.

After the contact mass is given catalytic activity as mentioned above, the organohalide is introduced into the reactor where gas-solid catalytic reaction takes place between the organohalide and metallic silicon to form organohalosilanes.

It is appreciated that the reaction is preferably effected at a temperature of about 230 to 600° C., and especially about 250 to 500° C. The reactor used herein may be a fluidized bed, stirred bed or fixed bed reactor though not limited thereto. From the industrial standpoint, a fluidized bed reactor capable of continuous operation is preferable.

EXAMPLE

Examples of the invention are given below by way of illustration and not by way of limitation. Parts are by weight.

Example 1

Figure 2:
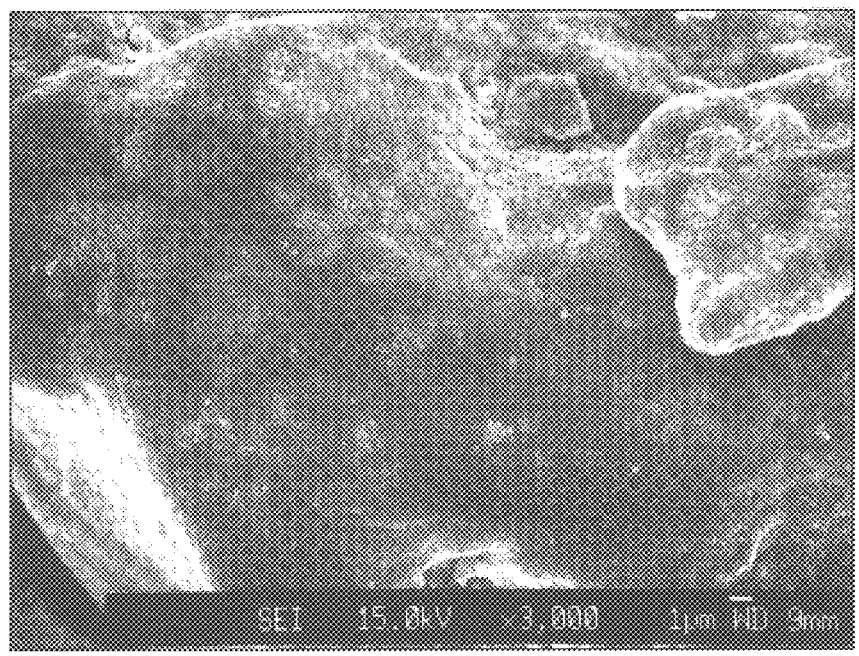
FIG. 2 is a SEM photomicrograph (×3000) of fumed silica-attached copper phosphide particles in Example 1.

Copper phosphide co-catalyst powder having a specific surface area of 0.06 $m^2/g$ and hydrophobic fumed silica having a specific surface area of 120 $m^2/g$ were mixed in a weight ratio of 100:1. Using a mechanofusion device AM-15F (by Hosokawa Micron Co., Ltd.), the mixture was rubbed in a nitrogen stream under conditions: agitating power 1.0 kW and casing revolution 1,200 rpm. After the mechanofusion treatment, the copper phosphide powder having fumed silica attached thereto had a specific surface area of 0.06 $m^2/g$. FIG. 2 is a photomicrograph under SEM of the powder. From the specific surface area and photomicrograph, it was ascertained that fumed silica had been fused to surfaces of copper phosphide particles as a result of high shear forces applied during the mechanofusion treatment.

Next, a reactor having an inner diameter of 50 mm and a height of 500 mm was charged with 100 parts of metallic silicon powder (Fe 0.26%, Al 0.13%, Ca 0.07%), 3 parts of electrolytic copper powder, 0.1 part of zinc powder, 0.005 part of tin powder, and 0.36 part of the copper phosphide powder having fumed silica attached thereto by mechanofusion treatment. Methyl chloride was fed to the reactor, and reaction was carried out under the following conditions:

reaction temperature: 310° C., reaction time: 6 hours, reactor internal pressure: 1.2 $kg/cm^2$, and gas flow rate: 0.7 NL/min. The results are shown in Table 1.

Comparative Example 1

A reactor having an inner diameter of 50 mm and a height of 500 mm was charged with 100 parts of metallic silicon powder (Fe 0.26%, Al 0.13%, Ca 0.07%), 3 parts of electrolytic copper powder, 0.1 part of zinc powder, 0.005 part of tin powder, and 0.36 part of copper phosphide co-catalyst powder. Methyl chloride was fed to the reactor, and reaction was carried out under the same conditions as in Example 1. The results are shown in Table 1. The formation rate representative of reactivity is low as compared with Example 1.

Comparative Example 2

Figure 3:
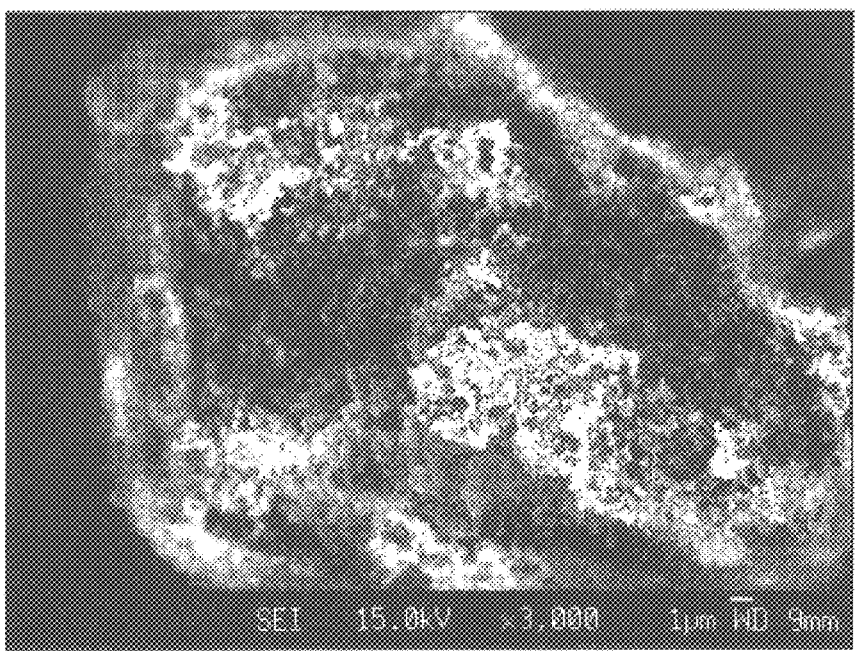
FIG. 3 is a SEM photomicrograph (×3000) of copper phosphide particles mixed with fumed silica in Comparative Example 2.

Copper phosphide co-catalyst powder having a specific surface area of 0.06 $m^2/g$ and hydrophobic fumed silica having a specific surface area of 120 $m^2/g$ were mixed in a weight ratio of 100:1. The copper phosphide powder having fumed silica admixed therewith had a specific surface area of 1.58 $m^2/g$. FIG. 3 is a photomicrograph under SEM of the powder. From the specific surface area and photomicrograph, it was ascertained that fumed silica was simply distributed on, but not fused to surfaces of copper phosphide particles as a result of mere mixing.

Next, a reactor having an inner diameter of 50 mm and a height of 500 mm was charged with 100 parts of metallic silicon powder (Fe 0.26%, Al 0.13%, Ca 0.07%), 3 parts of electrolytic copper powder, 0.1 part of zinc powder, 0.005 part of tin powder, and 0.36 part of the copper phosphide powder/fumed silica mixture. Methyl chloride was fed to the reactor, and reaction was carried out under the same conditions as in Example 1. The results are shown in Table 1. The formation rate was higher than in Comparative Example 1, but not so high as in Example 1.

Example 2

Copper phosphide co-catalyst powder having a specific surface area of 0.06 $m^2/g$ and hydrophobic fumed silica having a specific surface area of 120 $m^2/g$ were mixed in a weight ratio of 100:1. Using a mechanofusion device AM-15F (by Hosokawa Micron Co., Ltd.), the mixture was rubbed in a nitrogen stream under conditions: agitating power 1.0 kW and casing revolution 1,200 rpm.

Next, a reactor having an inner diameter of 50 mm and a height of 500 mm was charged with 100 parts of metallic silicon powder (Fe 0.26%, Al 0.13%, Ca 0.07%), 4 parts of copper oxide powder, 0.1 part of zinc powder, 0.005 part of tin powder, and 0.36 part of the copper phosphide powder having fumed silica attached thereto by mechanofusion treatment. Methyl chloride was fed to the reactor, and reaction was carried out under the following conditions:

reaction temperature: 320° C., reaction time: 6 hours, reactor internal pressure: 1.2 $kg/cm^2$, and gas flow rate: 0.7 NL/min. The results are shown in Table 1.

Comparative Example 3

A reactor having an inner diameter of 50 mm and a height of 500 mm was charged with 100 parts of metallic silicon powder (Fe 0.26%, Al 0.13%, Ca 0.07%), 4 parts of copper oxide powder, 0.1 part of zinc powder, 0.005 part of tin powder, and 0.36 part of copper phosphide co-catalyst powder. Methyl chloride was fed to the reactor, and reaction was carried out under the same conditions as in Example 2. The results are shown in Table 1. The formation rate representative of reactivity is low as compared with Example 2.

Comparative Example 4

Copper phosphide co-catalyst powder having a specific surface area of 0.06 $m^2/g$ and hydrophobic fumed silica having a specific surface area of 120 $m^2/g$ were mixed in a weight ratio of 100:1.

Next, a reactor having an inner diameter of 50 mm and a height of 500 mm was charged with 100 parts of metallic silicon powder (Fe 0.26%, Al 0.13%, Ca 0.07%), 4 parts of copper oxide powder, 0.1 part of zinc powder, 0.005 part of tin powder, and 0.36 part of the copper phosphide powder/fumed silica mixture. Methyl chloride was fed to the reactor, and reaction was carried out under the same conditions as in Example 2. The results are shown in Table 1. The formation rate was higher than in Comparative Example 3, but not so high as in Example 2.

Example 3

Electrolytic copper powder and hydrophobic fumed silica were mixed in a weight ratio of 100:1. Using a mechanofusion device AM-15F (by Hosokawa Micron Co., Ltd.), the mixture was rubbed in a nitrogen stream under conditions: agitating power 1.0 kW and casing revolution 1,200 rpm.

Next, a reactor having an inner diameter of 50 mm and a height of 500 mm was charged with 100 parts of metallic silicon powder (Fe 0.26%, Al 0.13%, Ca 0.07%), 3 parts of the electrolytic copper powder having fumed silica attached thereto by mechanofusion treatment, 0.1 part of zinc powder, and 0.005 part of tin powder. Methyl chloride was fed to the reactor, and reaction was carried out under the same conditions as in Example 1. The results are shown in Table 1.

Comparative Example 5

A reactor having an inner diameter of 50 mm and a height of 500 mm was charged with 100 parts of metallic silicon powder (Fe 0.26%, Al 0.13%, Ca 0.07%), 3 parts of electrolytic copper powder, 0.1 part of zinc powder, and 0.005 part of tin powder. Methyl chloride was fed to the reactor, and reaction was carried out under the same conditions as in Example 1. The results are shown in Table 1.

Comparative Example 6

Electrolytic copper powder and hydrophobic fumed silica were mixed in a weight ratio of 100:1. A reactor having an inner diameter of 50 mm and a height of 500 mm was charged with 100 parts of metallic silicon powder (Fe 0.26%, Al 0.13%, Ca 0.07%), 3 parts of the electrolytic copper powder/fumed silica mixture, 0.1 part of zinc powder, and 0.005 part of tin powder. Methyl chloride was fed to the reactor, and reaction was carried out under the same conditions as in Example 1. The results are shown in Table 1.

Example 4

Copper oxide powder and hydrophobic fumed silica were mixed in a weight ratio of 100:1. Using a mechanofusion device AM-15F (by Hosokawa Micron Co., Ltd.), the mixture was rubbed in a nitrogen stream under conditions: agitating power 1.0 kW and casing revolution 1,200 rpm.

Next, a reactor having an inner diameter of 50 mm and a height of 500 mm was charged with 100 parts of metallic silicon powder (Fe 0.26%, Al 0.13%, Ca 0.07%), 4 parts of the copper oxide powder having fumed silica attached thereto by mechanofusion treatment, 0.1 part of zinc powder, and 0.005 part of tin powder. Methyl chloride was fed to the reactor, and reaction was carried out under the same conditions as in Example 1. The results are shown in Table 1.

Comparative Example 7

A reactor having an inner diameter of 50 mm and a height of 500 mm was charged with 100 parts of metallic silicon powder (Fe 0.26%, Al 0.13%, Ca 0.07%), 4 parts of copper oxide powder, 0.1 part of zinc powder, and 0.005 part of tin powder. Methyl chloride was fed to the reactor, and reaction was carried out under the same conditions as in Example 2. The results are shown in Table 1.

Comparative Example 8

Copper oxide powder and hydrophobic fumed silica were mixed in a weight ratio of 100:1. A reactor having an inner diameter of 50 mm and a height of 500 mm was charged with 100 parts of metallic silicon powder (Fe 0.26%, Al 0.13%, Ca 0.07%), 4 parts of the copper oxide powder/fumed silica mixture, 0.1 part of zinc powder, and 0.005 part of tin powder. Methyl chloride was fed to the reactor, and reaction was carried out under the same conditions as in Example 2. The results are shown in Table 1.

TABLE 1

| | Reaction temperature (° C.) | Metallic silicon (pbw) | Electrolytic copper (pbw) | Copper oxide (pbw) | Zinc (pbw) | Tin (pbw) | Copper phoshide (pbw) | Fumed silica (pbw) | Formation rate (g-silane/h) | Composition M (%) | T (%) | D (%) |
|---|---|---|---|---|---|---|---|---|---|---|---|---|
| E1 | 310 | 100 | 3 | | 0.1 | 0.005 | 0.36 | 0.0036 | 45.9 | 1.08 | 4.00 | 92.0 |
| CE1 | 310 | 100 | 3 | | 0.1 | 0.005 | 0.36 | | 35.0 | 1.21 | 4.56 | 91.7 |
| CE2 | 310 | 100 | 3 | | 0.1 | 0.005 | 0.36 | 0.0036 | 36.2 | 0.97 | 3.94 | 92.8 |
| E2 | 320 | 100 | | 4 | 0.1 | 0.005 | 0.36 | 0.0036 | 50.1 | 1.19 | 3.90 | 92.5 |
| CE3 | 320 | 100 | | 4 | 0.1 | 0.005 | 0.36 | | 33.4 | 1.27 | 4.54 | 91.6 |

TABLE 1-continued

|  | Reaction temperature (°C.) | Metallic silicon (pbw) | Electrolytic copper (pbw) | Copper oxide (pbw) | Zinc (pbw) | Tin (pbw) | Copper phoshide (pbw) | Fumed silica (pbw) | Formation rate (g-silane/h) | Composition | | |
|---|---|---|---|---|---|---|---|---|---|---|---|---|
|  |  |  |  |  |  |  |  |  |  | M (%) | T (%) | D (%) |
| CE4 | 320 | 100 |  | 4 | 0.1 | 0.005 | 0.36 | 0.0036 | 38.9 | 1.28 | 4.41 | 92.0 |
| E3 | 310 | 100 | 3 |  | 0.1 | 0.005 |  | 0.03 | 47.1 | 1.50 | 6.57 | 86.7 |
| CE5 | 310 | 100 | 3 |  | 0.1 | 0.005 |  |  | 35.0 | 1.47 | 6.06 | 87.3 |
| CE6 | 310 | 100 | 3 |  | 0.1 | 0.005 |  | 0.03 | 37.0 | 1.43 | 6.68 | 86.8 |
| E4 | 320 | 100 |  | 4 | 0.1 | 0.005 |  | 0.04 | 48.2 | 1.44 | 5.95 | 87.9 |
| CE7 | 320 | 100 |  | 4 | 0.1 | 0.005 |  |  | 34.0 | 1.46 | 6.23 | 87.4 |
| CE8 | 320 | 100 |  | 4 | 0.1 | 0.005 |  | 0.04 | 38.6 | 1.47 | 6.34 | 87.2 |

The process for producing organohalosilanes according to the invention can increase the formation rate of organohalosilanes without reducing the proportion of diorganodihalosilane produced.

Japanese Patent Application No. 2000-320538 is incorporated herein by reference.

Reasonable modifications and variations are possible from the foregoing disclosure without departing from either the spirit or scope of the present invention as defined by the claims.

What is claimed is:

1. A process for preparing oganohalosilanes comprising the steps of charging a reactor with a contact mass containing a metallic silicon powder, a copper catalyst and a co-catalyst, and introducing an organohalide-containing gas into the reactor to effect reaction to form organohalosilanes of the following general formula (1):

$$R_n(H)_mSiX_{(4-n-m)} \quad (1)$$

wherein R is a monovalent hydrocarbon group of 1 to 6 carbon atoms, X is a halogen atom, n and m each are an integer of 0 to 3, and the sum of n and m is 1 to 3, said process further comprising the steps of mixing particles of the catalyst and/or co-catalyst with finely divided silica, and mechanically applying shear forces to the mixture for mutually rubbing the particles, thereby producing the catalyst and/or co-catalyst having finely divided silica attached to surfaces thereof, which is used in the contact mass.

2. The process of claim 1 wherein mechanical means for applying shear forces to the mixture for mutually rubbing the particles is selected from the group consisting of a mechanofusion device, ball mill, media agitating mill, planetary mill, high-speed rotary type grinding machine, jet mill, shear mill and roller mill.

3. The process of claim 1 wherein reaction is effected at a temperature of 230 to 600° C.

4. The process of claim 1 wherein the organohalide is methyl chloride or benzene chloride.

5. The process of claim 1 wherein the reactor is a fluidized bed, stirred bed or fixed bed reactor.

* * * * *